United States Patent [19]

Farber

[11] 4,022,771
[45] May 10, 1977

[54] AMINOPHENYL LACTONE COMPOUNDS CONTAINING AN ETHYLENO GROUP

[75] Inventor: Sheldon Farber, Appleton, Wis.

[73] Assignee: NCR Corporation, Dayton, Ohio

[22] Filed: Apr. 10, 1975

[21] Appl. No.: 566,852

[52] U.S. Cl. .................. 260/240 D; 260/240.1; 260/240 E; 260/313.1; 260/250 R
[51] Int. Cl.² ............ C07D 307/86; C07D 307/88
[58] Field of Search ........ 260/240 D, 240 E, 240.1; 427/151

[56] References Cited

UNITED STATES PATENTS

| | | | |
|---|---|---|---|
| 2,505,488 | 4/1950 | Green | 427/151 |
| 3,703,397 | 11/1972 | Lin et al. | 260/240.1 X |
| 3,896,116 | 9/1975 | Ozutsumi et al. | 260/240 D |
| 3,928,685 | 12/1975 | Alsop | 260/240 D X |

Primary Examiner—Allen B. Curtis
Attorney, Agent, or Firm—E. Frank McKinney

[57] ABSTRACT

A chromogenic compound of normally colorless form is disclosed having the following structural formula:

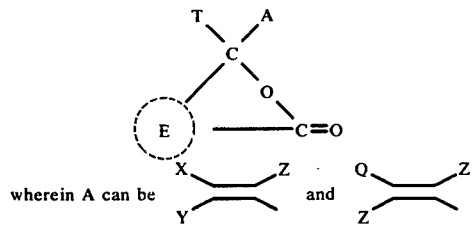

T, Q, X, Y and Z can be, among several others, hydrogen, alkyl, alkoxy, aryl, and heterocyclic, substituted and unsubstituted; and E can be a broad family of aromatic and heterocyclic structures. The compound is eligible for use in pressure-sensitive record materials and manifold marking systems. Because of light absorption characteristics, selected compounds of this invention are especially useful where machine readability and machine copiability are important.

12 Claims, 4 Drawing Figures

AMINOPHENYL LACTONE COMPOUNDS CONTAINING AN ETHYLENO GROUP

BACKGROUND OF THE INVENTION

1. Field of the Invention

This invention pertains to colorable chromogenic compounds eligible for use in pressure-sensitive record material. Pressure-sensitive mark-forming record systems, single sheet and manifold, are improved by use of these compounds.

More specifically, this invention relates to chromogenic compounds having one vinyl linkage which compounds have the form of substantially colorless or slightly colored solids, or which approach being colorless when in liquid solution; but, which may be converted to dark-colored forms upon reactive contact with acidic material. As used in mark-forming systems, marking in desired areas on support webs or sheets may be accomplished by effecting localized reactive contact between the chromogenic material and the acidic material on or in such web or sheet, such material being brought thereto by transfer, or originally there in situ, the desired reactive contact forming dark-colored materials in the intended image-marking areas.

The chromogenic compounds of this invention have the following general formula:

T, Q, X, Y, and Z can be, among several others, hydrogen, alkyl, alkoxy, aryl, and heterocyclic, substituted and unsubstituted; and E can be a broad family of aromatic and heterocyclic structures.

The chromogenic compounds of this invention especially relate to marks at or near the near infrared part of the color spectrum; and, in that regard, especially relate to providing a color which is particularly visible to machine readers and copiers.

2. Description of the Prior Art

Several phthalide and fluoran chromogenic compounds have been disclosed. For example, U.S. Pat. Nos. 3,491,111 and 3,491,116, issued Jan. 20, 1970, disclose indole- and carbazol-substituted phthalides. U.S. Pat. No. 2,417,897, issued Mar. 25, 1947, discloses crystal violet lactone. U.S. Pat. No. 3,681,390, issued Aug. 1, 1972, discloses aryl-substituted fluorans.

U.S. Pat. No. 3,672,935, issued June 27, 1972, discloses use of colorless chromogenic compounds in pressure-sensitive record material.

G. Hallas, in the *Journal of the Society of Dyers and Colourists*, in September, 1967, at pages 368 to 373 and in June, 1970, at pages 237–242 discusses the effects of extended conjugation on colored dye compounds.

SUMMARY OF THE INVENTION

Colorable chromogenic compounds having one vinyl linkage have been discovered which compounds are initially substantially colorless but produce dark-colored products on reaction with certain acid materials. The vinyl-containing chromogenic compounds exhibit light absorption, in the colored form, at wavelengths nearer to infrared than chromogenic compounds without vinyl groups. It is an object of this invention to provide such vinyl-containing compounds and methods for making them.

An important use for the vinyl compounds of this invention resides in their incorporation into pressure-sensitive record systems as a colorable reactant for development of color on application of a mark-forming force. Hence, it is an object of this invention to provide substances having near infrared color response and chromogenic properties, which substances can be incorporated in a web or coated onto the surface of a web to provide a record sheet or a manifolding unit, and which are useful in carrying out methods of marking involving reactive contact with a color-activating material to develop dark-colored materials in areas where marking is desired.

It is an object of this invention to provide modified compounds, based upon the aforementioned vinyl-containing compounds, which are substantially colorless, or slightly colored, offering a variety of chromogenic characteristics, and developing dark-colored substances absorbing at increased wavelengths upon contact with color-activating materials.

BRIEF DESCRIPTION OF THE DRAWING

The chromogenic compounds of this invention include a large variety of several moieties with the vinyl linkages and lactone rings being necessarily common to all. In order to more completely and more distinctly disclose the variety of moiety combinations which forms a part of this invention, a drawing is included which is a schematic representation of the combinations, by structural formula.

Also included as drawings, are graphic representations of the absorption spectra of compounds of this invention compared with the spectra of similar compounds from the prior art.

Figure 1:
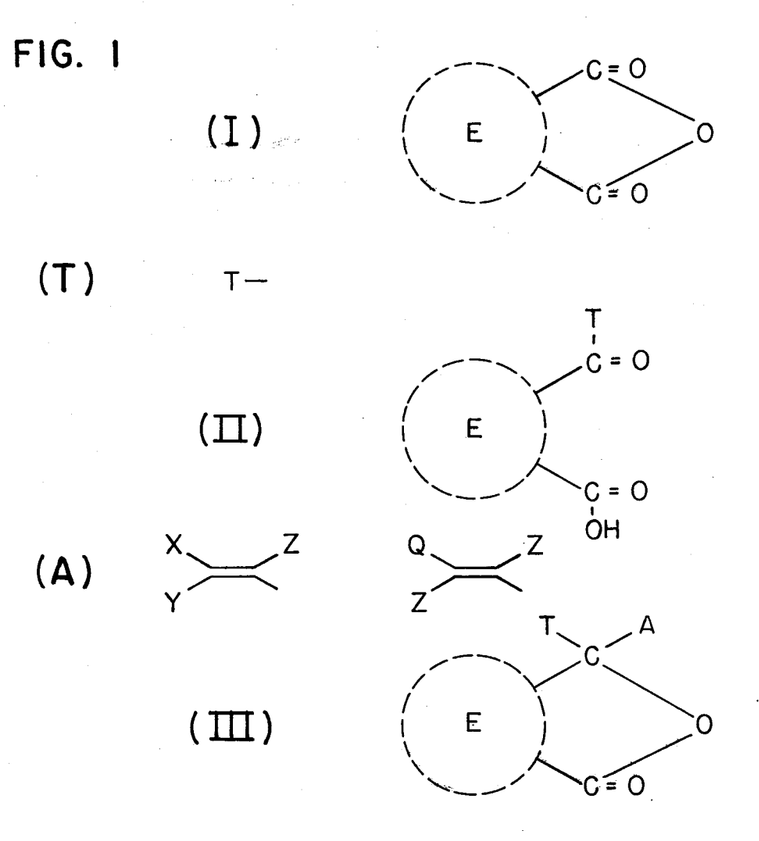

The drawing represents a figurative, schematic, step-by-step structural development of the vinyl-containing compounds of this invention, as they can be prepared. A dicarboxylic anhydride (I) is combined with a substrate reactant (T) to yield a keto acid (II), which is, in turn, combined with a vinyl-containing substrate reactant (A) to yield the chromogenic compound (III) of this invention. The structural development shown is not necessarily a representation of the actual compound synthesis. The synthetic process is not embraced as a part of this invention.

The dicarboxylic anhydride (I), in FIG. 1, includes E as the supporting molecular structure. E represents a large variety of structures including aromatic and heterocyclic, substituted and unsubstituted. The substitutions include halo, nitro, cyano, and alkylthio, alkoxy, alkyl, monoalkylamino and dialkylamino with alkyl of less than seven carbon atoms. Halogen or halo-, in this invention, means fluorine, chlorine, bromine and iodine. (I) is not required to be a dicarboxylic anhydride. A dicarboxylic acid will suffice if the keto acid-forming reaction is conducted under dehydrating conditions such as in acetic anhydride. Moreover, the vinyl-containing compound (A) can be a methyl carbinol under dehydrating conditions.

Figuratively speaking and in accord with the drawing, substrate moieties are added to the supporting molecular structure and at least one of the substrate moieties must contain a vinyl linkage. Substrate moieties are addd at (T) to yield (II), a keto acid; and at (A) to yield (III), the compound of this invention.

(A) provides structural, schematic, indication of the manner in which vinyl linkages are introduced into the compounds of this invention. While there are differences between the specific moieties which will be disclosed in detail, below, it suffices to say, here, that X, Y, and Z represent, among other things, substituted and unsubstituted aromatic and heterocyclic groups as a part of the moieties of (A). Additionally, Q is exclusively a nitrogen heterocyclic and is joined to a carbon of the vinyl double bond at the nitrogen.

Figure 2:
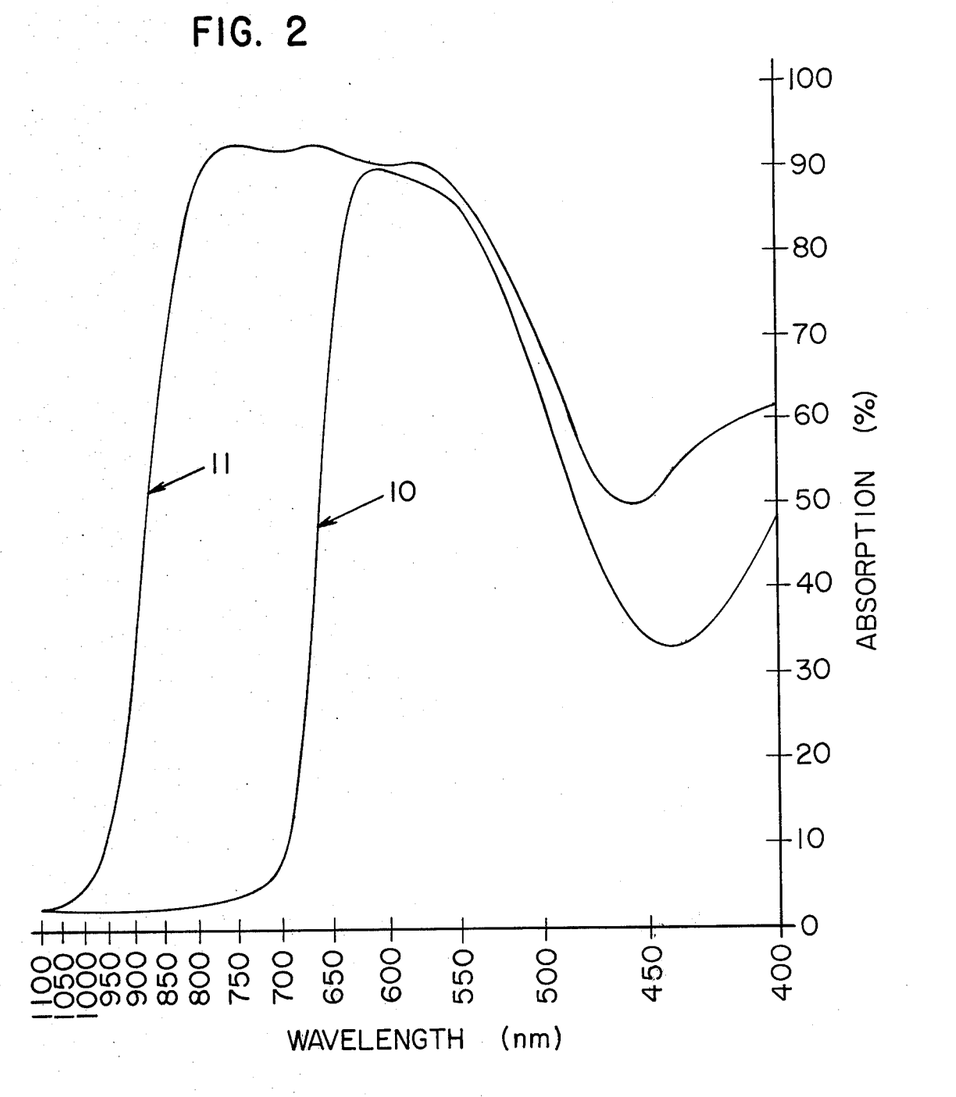
Figure 3:
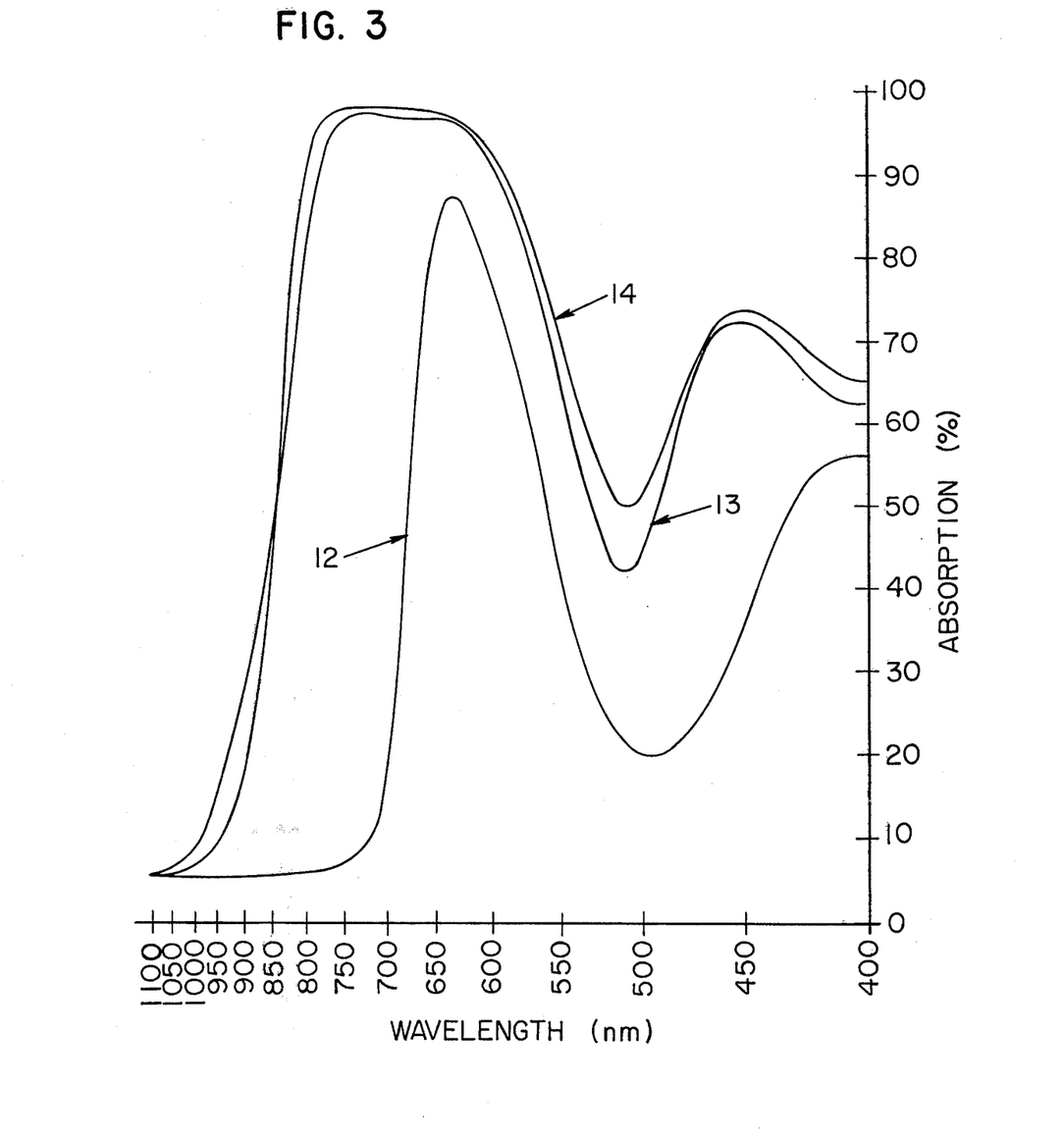
Figure 4:
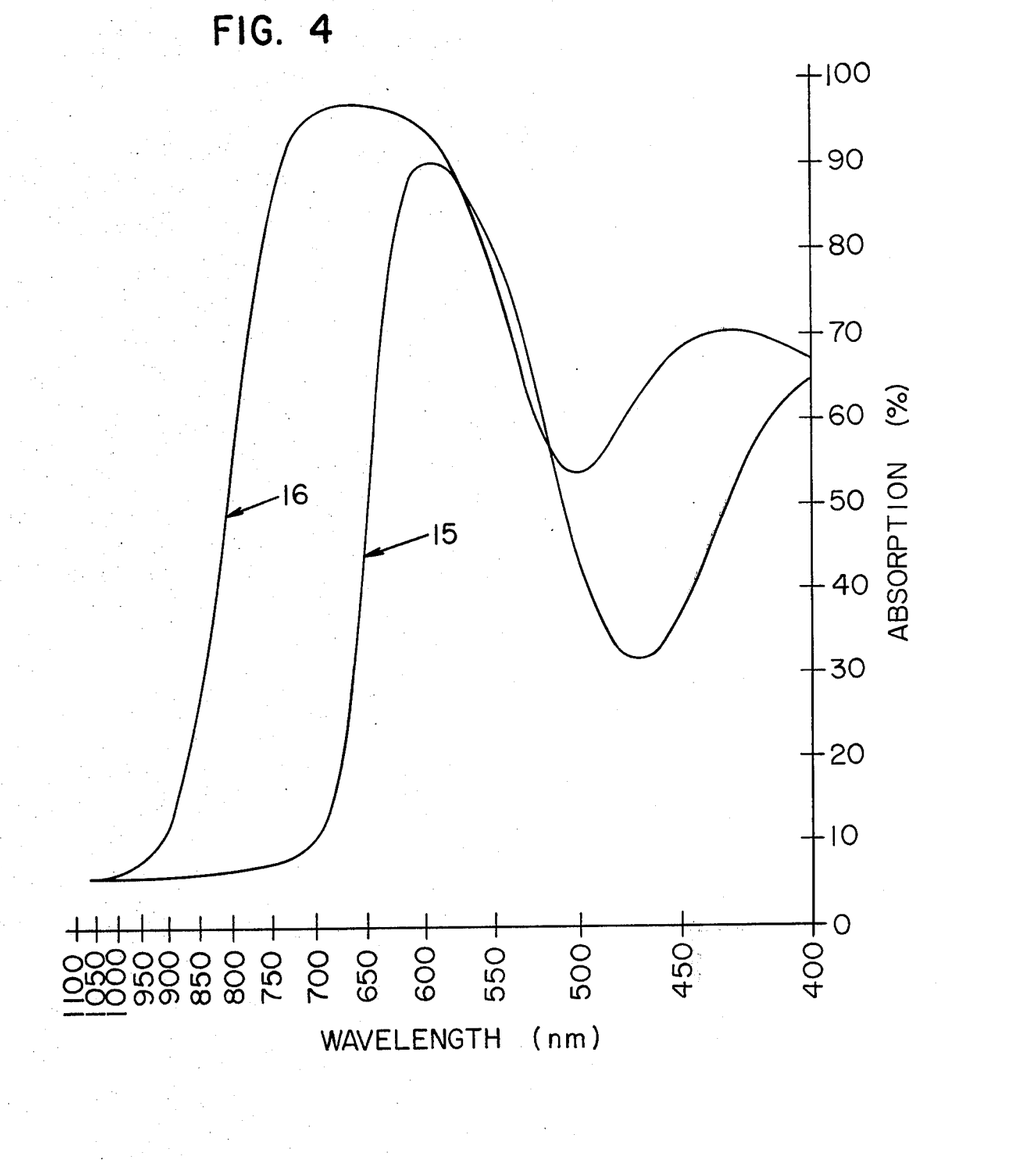

FIGS. 2 through 4 are comparative showings of the difference between reflectance of the colored form of the vinyl-containing compounds of this invention and the reflectance of similar compounds, but without the vinyl linkage, from the prior art. The abscissa in those graphical showing represents wavelength on a reciprocal scale and the ordinate represents percent of incident light absorbed. Throughout the consideration of this invention, it should be kept in mind that light visible to the human eye exists from about 400 to 700 nanometers wavelength and machine readers and copiers exhibit a maximum sensitivity at about 830 nanometers. FIGS. 2 through 4 indicate that, without exception, those compounds of this invention are remarkably more absorbent of light in the machine reading range than are prior art compounds.

The curves of FIGS. 2 through 4 represent the light absorption characteristics of selected chromogenic compounds, in colored form, as reacted from solution on a paper coated with a phenolic resin. In each figure, vinyl color formers of this invention are placed in comparative relation to compounds of the prior art having similar molecular structure or similar visible color; but without the vinyl element.

FIG. 2 is a comparison of the absorption spectrum of 3,3-bis-(4-dimethylaminophenyl)-6-(dimethylamino)phthalide (10), also known as crystal violet lactone, with the absorption spectrum of 3-(4-dimethylaminophenyl)-3-[bis-1,1-(p-dimethylaminophenyl)-ethyleno-2]-6-dimethylamino phthalide (11), from Example 4, herein. The crystal violet lactone curve (10) has an absorption peak at about 625 nanometers (nm) which slopes to an ill-defined shoulder at about 515 nm and has strong absorption character between about 650 and 510 nm. In contrast, the 3-(4-dimethylaminophenyl)-3-[bis-1,1-(p-dimethylaminophenyl)-ethyleno-2]-6-dimethylaminophthalide curve (11) has an absorption peak at about 770 nm and strong secondary peaks at about 670 nm and 575 nm; and has strong absorption character between about 850 and 510 nm.

FIG. 3 is a comparison of the absorption spectrum of 3,3-bis-(4-dimethylaminophenyl)phthalide (12), also known as malachite green lactone, with the absorption spectra of 3-(4-diethylaminophen-1-yl)-3-[bis-1,1-(p-diethylaminophenyl)-ethyleno-2]phthalide (13), from Example 1, herein, and 3-(2-methoxy-4-diethylaminophenyl)-3-[bis-1,1-(p-diethylaminophenyl)-ethyleno-2]phthalide (14), from Example 3, herein. The curve (12) has a rather sharp peak at about 640 nm while each of the curves (13) and (14) have a broad peak which extends from about 750 to about 640 nm.

FIG. 4 is a comparison of the absorption spectrum of 3-(1-ethyl-2-methylindol-3-yl)-3-(4-diethylaminophenyl)phthalide (15) with the absorption spectrum of 3-(1-ethyl-2-methylindol-3-yl)-3-[bis-1,1-(p-dimethylaminophenyl)ethyleno-2]phthalide (16), from Example 8, herein. The curve (15) has a relatively sharp peak at about 590 nm while the curve (16) has a broad peak from about 700 to about 630 nm.

DETAILED DESCRIPTION OF THE INVENTION

It should be remembered that what is considered to be an essential element of the invention herein is the presence of a vinyl linkage in a colorless but colorable chromogenic material. At the present time, the chromogenic compounds of this invention enjoy extensive eligibility for use in pressure-sensitive and thermally-sensitive mark-forming systems. Pressure-sensitive mark-forming systems provide a marking system of disposing on and/or within sheet support material unreacted mark-forming components and a liquid solvent in which each of the mark-forming components is soluble. The liquid solvent is present in such form that it is maintained isolated, by a pressure-rupturable barrier, from at least one of the mark-forming components until application of pressure causes a breach of the barrier in an area delineated by the pressure pattern. The mark-forming components are thereby brought into reactive contact, producing a distinctive mark.

The method of marking comprises providing a chromogenic compound selected from among the above-mentioned compounds and bringing such chromogenic compound into reactive contact, in areas where marking is desired, with an acidic color-activating substance to produce a dark-colored form of the chromogenic compound.

The acidic materials can be any compound within the definition of a Lewis acid, i.e., an electron acceptor. Preferably, acidic organic polymers such as phenolic polymers are employed as the acidic material. It is noted that the polymeric mark-forming components should have a common solubility with the chromogenic compound in at least one liquid solvent when the acid-reacting material is a phenolic or other organic acidic polymer. It is also noted that in a single system several chromogenic compounds can be used with the same or different polymeric materials. Several polymeric materials can be reactively contacted with a single chromogenic compound or with a mixture of chromogenic compounds.

The acidic polymeric material useful in this invention includes phenol polymers, phenol acetylene polymers, alkyl-phenolacetylene polymers, maleic acid-rosin resins, partially or wholly hydrolyzed styrene-maleic anhydride copolymers and ethylene-maleic anhydride copolymers, carboxy polymethylene and wholly or partially hydrolyzed vinyl methyl ether maleic anhydride copolymers and mixtures thereof.

When the acidic material is one of the aforementioned organic polymers, the liquid solvent chosen must be capable of dissolving the mark-forming components. The solvent can be volatile or non-volatile, and a single or multiple component solvent may be used which is wholly or partially volatile. Examples of volatile solvents useful in the aforedescribed basic chromogen-acidic polymer are toluene, petroleum distillate, perchloroethylene, xylene, and the like. Examples of non-volatile solvents are high-boiling point petroleum fractions, dioctyl adipate, biphenyls, diphenyl alkanes, and the like.

Generally, the solvent chosen should be capable of dissolving at least 0.3 percent, by weight, of the chromogenic compounds and at least about 3–5 percent, by weight, of the polymeric material. A further criterion of the solvent is that it must not interfere with the mark-forming reaction.

The support member on which the components of the system are disposed may comprise a single or dual sheet assembly. In the case where all components are disposed on a single sheet surface, the record material is referred to as a "self-contained" system. Where there must be a migration of the solvent, with or without mark-forming component, from one sheet to another, the record material is referred to as a "transfer" system. (Such a system can also be referred to as a "two-fold" system, in that at least two sheets are required and each sheet includes a component, or components, essential to the mark-forming reaction.) Where a copious amount of the colored reaction product in liquid form is produced on a surface of one sheet, it can produce a mark by transfer to a second sheet as a colored mark.

The polymeric material can be dissolved in ink composition vehicles to form a printing "ink" of colorless character and, thus, can be used to spot-print a proposed record sheet unit sensitized for recording in a reaction-produced color in those areas by application of a solution of the chromogenic material. In the case of phenolic polymer, a printing ink can be made of up to 75 percent, by weight, of the phenolic polymeric material in a petroleum solvent to a viscosity suitable for printing purposes.

In the mark-forming system herein, the acidic mark-forming component(s) reacts with the chromogenic material(s) to effect distinctive color formation or color change. In a multi-sheet system in which an acid organic polymer is employed, it is desirable to include other materials to supplement the reactants. For example, kaolin can be added to improve the transfer of the liquid and/or the dissolved materials between the sheets. In addition, other materials such as bentonite, attapulgite, talc, feldspar, halloysite, magnesium trisilicate, silica gel, pyrophyllite, zinc sulfide, calcium sulfate, calcium citrate, calcium phosphate, calcium fluoride, barium sulfate and tannic acid can be included. It should be noted that mineral materials such as kaolin, attapulgite, silica gel, silton clay, and the like can, also, be used alone or in combination with other materials as an acidic material coreactant.

Various methods known to the prior art and disclosed in the aforementioned U.S. Pat. No. 3,672,935 can be employed in coating compositions of the mark-forming materials into their supporting sheets. An example of the compositions which can be coated onto the surface of an underlying sheet of a two-sheet system to react with the chromogenic material on the underside of any overlying sheet is as follows:

| Coating Composition | Percent by Weight |
|---|---|
| Phenolic polymer mixture | 17 |
| Paper coating kaolin (white) | 57 |
| Calcium carbonate | 12 |
| Styrene butadiene latex | 4 |
| Ethylated starch | 8 |
| Gum arabic | 2 |
| | 100 |

Thermally-sensitive mark-forming systems can also be prepared using the compounds of this invention.

The compounds of this invention can be prepared as will be discussed in the examples which follow. Referring again, to FIG. 1;—E can be the following:

unsubstituted, and alkyl-, chloro-, dichloro-, trichloro-, tetrachloro-, bromo-, dibromo-, tribromo-, tetrabromo-, nitro-, and dialkylamino-substituted;

unsubstituted and nitro-substituted;

E can also be aromatic single anhydride residues such as result from homophthalic anhydride and biphenyl-4,4'-dicarboxylic anhydride

T can be the following:

and wherein $R_1$ and $R_2$ are hydrogen, alkyl, substituted phenyl, unsubstituted phenyl, benzyl, cycloalkyl, and acyl; $R_3$, $R_4$, $R_5$ and $R_6$ are hydrogen, alkyl, aryl, alkoxy, halo, aralkyl, dialkylamino, monoalkylamino, amino, acylamino, mercapto, and alkylthio; and $R_7$ and $R_8$ are hydrogen, phenyl and alkyl. $R_1$ and $R_2$ are not both phenyl.

Q can be the following:

X can be the following:

wherein the R designations are the same as those earlier for T.

Y can be any X, hydrogen, and carbalkoxy.

Z can be hydrogen, halo, alkyl, carbalkoxy, benzyl, substituted phenyl, unsubstituted phenyl, and pyridino.

X or Y or both can also be 4-alkoxyphenyl; 2,4-dialkoxyphenyl; and 3,4-dialkoxyphenyl.

It should be understood that "alkyl" and any group requiring alkyl, such as "alkoxy" or "dialkylamino" means methyl, ethyl propyl (including isopropyl), butyl (including isobutyl and tert-butyl), pentyl (including all five-carbon isomers), hexyl (including all six-carbon isomers), and the like having less than seven carbon atoms.

This invention is further illustrated by the following examples. The reactants and the proportions and other specific conditions are represented as being typical and should not be construed to limit the invention.

DESCRIPTION OF THE PREFERRED EMBODIMENTS

In the following examples, general procedures for preparing certain compounds of this invention are disclosed; and the procedures are followed by summaries of additional compounds prepared in the same manner. The summaries are not intended to be exhaustive and it must be remembered that the moieties, as previously defined, are all eligible for use in any combination in preparing the compounds.

EXAMPLE 1

Preparation of 3-(4-diethylaminophen-1-yl)-3-[bis-1,1-p-diethylaminophenyl)-ethyleno-2]phthalide.

With reference to the drawing in respect of this example and like examples which follow, the description of compound preparation commences at (II), the keto-acid, because preparation of the keto-acid is known or not difficult. For instance, the keto-acid of this example is easily prepared, either by mol-for-mol combination of phthalic anhydride (I) and N,N-diethylaniline (T), in the presence of a catalyst such as aluminum chloride or other Friedel-Crafts catalysts and in a solvent such as methylene chloride, or by the reaction of phthalic anhydride with m-diethylaminophenol followed by reaction of the keto-acid, thus obtained with dimethyl sulfate to etherify the hydroxyl group.

For ease in understanding, the Examples are summarized in listings of components, the (T) components are listed as radicals, and the (A) components are listed as compounds. Such listing is believed to facilitate comprehension of the molecular structures.

Combining the appropriate keto-acid, 2-(4-diethylaminobenzoyl) benzoic acid (II), with an appropriate ethylene base, results in a compound of this invention. This example will be given with details of the reaction conditions and will be followed by an additional listing of exemplary compounds. A mixture of 3.0 grams of the keto-acid (moiety II from I and T), 3.2 grams of bis-1,1-(p-diethylaminophenyl)ethylene (moiety A, wherein X and Y are p-diethylaminophenyl and Z is hydrogen), and 15 milliliters of acetic anhydride is refluxed for sixty minutes and poured into ice and ammonia. The system is extracted with toluene, dried in the toluene using sodium sulfate, and the toluene is evaporated. The residue is dissolved in toluene and chromatographed on alumina. The compound is eluted using toluene and is recrystallized from toluene-petroleum ether and then from toluene-heptane. The product exhibits a melting point of 122°–124° centigrade and a solution of the product imparts a greenish-blue color to paper coated with a phenolic resin or silton clay or a combination of the two. A reflectance spectrum of the greenish-blue color has unresolved absorption peaks at 750 and 660 nanometers. The calculated analysis for $C_{40}H_{47}N_3O_2$, the title compound, is C, 79.83%; H, 7.87%; and N, 6.98%. Found, on analysis: C, 79.72%; H, 7.76%; and N, 7.15%.

This example is also conducted using bis-1,1-(p-di-t-butylaminophenyl)ethylene, bis-1,1-(2-ethoxy-4-dimethylaminophenyl)ethylene, bis-1,1-(2-methyl-4-diethylaminophenyl)ethylene or 2-ethyl-bis-1,1-(p-dimethylaminophenyl)ethylene. It should be pointed out that many of the ethylene compounds themselves are chromogenic compounds.

This example is also conducted using other anhydrides, such as 2,3-naphthalene dicarboxylic acid anhydride, as the (I) moiety.

Example 1, Summarized.
(I)  phthalic anhydride
    (T)  p-diethylaminophenyl
        (A)  bis-1,1-(p-diethylaminophenyl)ethylene
            green-blue. absorption peak at 750 nanometers
        (A)  bis-1,1-(p-methoxyphenyl)ethylene
            orange. absorption peak at 650 nanometers
  also  (A)  bis-1,1-(p-di-t-butylaminophenyl)ethylene
  also  (A)  bis-1,1-(2-ethoxy-4-dimethylaminophenyl)ethylene
  also  (A)  2-ethyl-bis-1,1-(p-dimethylaminophenyl)ethylene
        (A)  bis-1,1-(p-dimethylaminophenyl)ethylene
            green-blue. absorption peak at 770 nanometers
        (A)  2-carbethoxy-bis-1,1-(p-dimethylaminophenyl)ethylene
            green. absorption peak at 640 nanometers
  also  (A)  2-benzyl-bis-1,1-(p-dimethylaminophenyl)ethylene
        (A)  2-methyl-bis-1,1-(p-diethylaminophenyl)ethylene
            green. absorption peak at 660 nanometers
        (A)  2-phenyl-bis-1,1-(p-dimethylaminophenyl)ethylene
            green. absorption peak at 660 nanometers
        (A)  bis-1,1-(2-methyl-4-diethylaminophenyl)ethylene
            absorption peak at 770 nanometers
    (T)  p-dimethylaminophenyl
        (A)  2-phenyl-bis-1,1-(p-dimethylaminophenyl)ethylene
            green. absorption peak at 660 nanometers
    (T)  2-methoxy-4-diethylaminophenyl
        (A)  2-methyl-bis-1,1-(p-dimethylaminophenyl)ethylene
            blue-green. absorption peak at 630 nanometers
        (A)  bis-1,1-(p-methoxyphenyl)ethylene
            orange. absorption peak at 600 nanometers
        (A)  bis-1,1-(2-methyl-4-diethylaminophenyl)ethylene
            green. absorption peak at 750 nanometers
        (A)  2-carbethoxy-bis-1,1-(p-dimethylaminophenyl)ethylene
            olive. absorption peak at 650 nanometers
    (T)  1-(N,4'-dimethyl-2-methoxydiphenylamino)
        (A)  bis-1,1-(p-methoxyphenyl)ethylene
            red. absorption peak at 570 nanometers
  also  (T)  2-butyoxy-4-diethylaminophenyl
    also  (A)  2-methyl-bis-1,1-(p-dipropylaminophenyl)ethylene
    also  (A)  bis-1,1-(2-methyl-4-diethylaminophenyl)ethylene
    (T)  2-methoxy-4-cyclohexylaminophenyl
        (A)  bis-1,1-(2-methyl-4-diethylaminophenyl)ethylene
            green. absorption peak at 725 nanometers
        (A)  bis-1,1-(p-methoxyphenyl)ethylene
            yellow. absorption peak at 600 nanometers
        (A)  2-carbethoxy-bis-1,1-(p-dimethylaminophenyl)ethylene
            green. absorption peak at 650 nanometers
  also  (T)  p-phenylaminophenyl
    also  (A)  bis-1,1-(p-phenylaminophenyl)ethylene
  also  (T)  benzylaminophenyl
    also  (A)  bis-1,1-(p-benzylaminophenyl)ethylene
    (T)  2-methoxy-4-dimethylaminophenyl
        (A)  2-phenyl-bis-1,1-(p-dimethylaminophenyl)ethylene
            yellow-blue. absorption peak at 660 nanometers
    (T)  1-(N,4'-dimethyl-2-methoxydiphenylamino)
        (A)  2-carbethoxy-bis-1,1-(p-dimethylaminophenyl)ethylene
            green. absorption peak at 650 nanometers
    also  (A)  bis-1,1-(2-methyl-4-diethylaminophenyl)ethylene
also (I) 2,3-naphthalene dicarboxylic acid anhydride
also (I) 1,8-naphthalene dicarboxylic acid anhydride
also (I) 4-nitro-1,8-naphthalene dicarboxylic acid anhydride
also (I) 3-nitro-phthalic anhydride

EXAMPLE 2

I. phthalic anhydride
T. 2-methoxy-4-diethylaminophenyl
A. bis-1,1-(p-diethylaminophenyl)ethylene green-blue, absorption peak at 770 nanometers Example 2, above, discloses an example of a compound of this invention which can be made by using a carbinol as well as by using an ethylene base. In preparing that compound using a carbinol, equimolar amounts of 2'-carboxy-2-methoxy-4-diethylaminobenzophenone and bis-1,1-(diethylaminophenyl)methyl carbinol are refluxed together in acetic anhydride and are isolated, as previously disclosed.

EXAMPLE 3

Preparation of 3-(4-dimethylaminophenyl)-3-[bis-1,1-(p-dimethylaminophenyl)-ethyleno-2]-6-dimethylaminophthalide.

The keto-acid for this example is 2-(4-dimethylaminobenzoyl)-5-dimethylaminobenzoic acid. A solution of 13.0 grams of the keto-acid 15.0 grams of bis-1,1-(p-dimethylaminophenyl)ethylene (moiety A, where X and Y are p-dimethylaminophenyl and Z is hydrogen), and 100 milliliters of acetic anhydride is stirred for about 1 hour at about 54° centigrade. The reaction mixture is poured into ice and ammonia and the product is extracted using toluene. The toluene solution is washed with saturated aqueous sodium sulfate solution; and is then filtered and the toluene evaporated. The residue is chromatographed and the product exhibits a melting point of 155°–158° centigrade. After further purification by recrystallization from toluene-petroleum ether, the material exhibits a melting point of 157°–159° centigrade. A solution of that product imparts a dark blue color to paper coated with a phenolic resin or silton clay or a combination of the two. A reflectance spectrum of the blue color has an absorption peak at about 770 nanometers. The calculated analysis for $C_{36}H_{40}N_4O_2$, the title compound is C, 77.24%; H, 7.12%; and N, 9.85%. Found, on analysis, C, 77.11%; H, 7.19%; and N, 9.99%.

Example 3, Summarized.
```
(I)      4-dimethylaminophthalic anhydride
         (T)     p-dimethylaminophenyl
                 (A)    bis-1,1-(p-dimethylaminophenyl)ethylene
                        blue. absorption peak at 770 nanometers
                 (A)    bis-1,1-(2-methyl-4-diethylaminophenyl)ethylene
                        blue. absorption peak at 770 nanometers
                 (A)    2-phenyl-bis-1,1-(p-dimethylaminophenyl)ethylene
                        blue. absorption peak at 660 nanometers
                 (A)    2-carbethoxy-bis-1,1-(p-dimethylaminophenyl)ethylene
                        absorption peaks at 655 and 590 nanometers
                 (A)    2-methyl-bis-1,1-(p-diethylaminophenyl)ethylene
                        green. absorption peak at 650 nanometers
                 (A)    bis-1,1-(p-methoxyphenyl)ethylene
                        blue. absorption peak at 675 nanometers
also (I) 4-di-t-butylamino phthalic anhydride and
         4-dihexylaminophthalic anhydride
   also  (T)     p-diethylaminophenyl
   also  (T)     p-aminophenyl
   also  (T)     2-hexyl-4-dihexylaminophenyl
         also   (A)     2-phenyl-bis-1,1-(p-dimethylaminophenyl)ethylene
         also   (A)     2-carbobutoxy-bis-1,1-(p-dimethylaminophenyl)ethylene
         also   (A)     bis-1,1-(2,4-di-dimethylaminophenyl)ethylene
         also   (A)     bis-1,1-(2-methylamino-4-dimethylaminophenyl)ethylene
         also   (A)     bis-1,1-(2-amino-4-dimethylaminophenyl)ethylene
         also   (A)     bis-1,1-(2-acetamino-4-dimethylaminophenyl)ethylene
```

EXAMPLE 4

Preparation of 3-(4-dimethylaminophenyl)-3-[bis-1,1-(p-dimethylaminophenyl)-ethyleno-2]-4,5,6,7-tetrachlorophthalide.

The keto acid for this example is 2-(4-dimmethylaminobenzoyl)-3,4,5,6-tetrachlorobenzoic acid and it is substituted mol-for-mol for the keto acid of Example 3, above. The conditions and other materials remain the same from Example 3. The keto acid is also prepared from phthalic anhydride which is mono-, di-, and tri-halo substituted rather than tetra-substituted; and bromine can be used rather than chlorine.

EXAMPLE 5

Preparation of 1-(2-chloro-4-diethylaminophenyl)-1-[bis-1,1-(p-dimethylaminophenyl)-ethyleno-2]-1-[H]-3-[H]-furo[3,4-b]-quinoxalin-3-one.

The keto acid for this example is 2-(2-chloro-4-diethylaminobenzoyl)-3-quinoxalinic acid; and it is disclosed as Preparation C of U.S. patent application Ser. No. 468,112, filed May 8, 1974. Reaction of that keto acid with an appropriate ethylene base, as previously described above, results in compounds of this invention. Reaction with bis-1,1-(p-dimethylaminophenyl)ethylene results in the title compound.

Example 4, Summarized.
```
(I)      3,4,5,6-tetrachlorophthalic anhydride
         (T)    p-dimethylaminophenyl
                (A)    bis-1,1-(p-dimethylaminophenyl)ethylene
                       green-blue. absorption peak at 770 nanometers
                (A)    2-methyl-bis-1,1-(p-diethylaminophenyl)ethylene
                       blue. absorption peak at 640 nanometers
                (A)    2-phenyl-bis-1,1-(p-dimethylaminophenyl)ethylene
                       green. absorption peak at 660 nanometers
                (A)    2-carbethoxy-bis-1,1-(p-dimethylaminophenyl)ethylene
                       green. absorption peak at 675 nanometers
                (A)    bis-1,1-(2-methyl-4-diethylaminophenyl)ethylene
                       green. absorption peak at 795 nanometers
                (A)    bis-1,1-(p-methoxyphenyl)ethylene
                       blue. absorption peak at 670 nanometers
also     (T)    2-chloro-4-diethylaminophenyl
also     (T)    p-diethylaminophenyl
         (T)    2-methoxy-4-diethylaminophenyl
                (A)    2-methyl-bis-1,1-(p-diethylaminophenyl)ethylene
                       green. absorption peak at 650 nanometers
                (A)    bis-1,1-(2-methyl-4-diethylaminophenyl)ethylene
                       green. absorption peak at 770 nanometers
                (A)    bis-1,1-(p-methoxyphenyl)ethylene
                       green. absorption peak at 660 nanometers
                (A)    2-carbethoxy-1,1-(p-dimethylaminophenyl)ethylene
                       green. absorption peak at 650 nanometers
```

Example 5, Summarized.
```
(I)          quinoxalinic anhydride
             (T)      2-chloro-4-diethylaminophenyl
                      (A)    bis-1,1-(p-dimethylaminophenyl)ethylene
                             yellow. absorption peak at 700 nanometers
                      (A)    bis-1,1-(2-methyl-4-diethylaminophenyl)ethylene
                             yellow. absorption peak at 690 nanometers
      also   (T)      2-hexoxy-4-dimethylaminophenyl
      also   (T)      2-phenyl-4-dimethylaminophenyl
             also     (A)    2-hexyl-bis-1,1-(p-diethylaminophenyl)ethylene
             also     (A)    2-phenyl-bis-1,1-(p-diethylaminophenyl)ethylene
             also     (A)    bis-1,1-(pyrrol-3-yl)ethylene and bis-1,1-(pyrrol-2-
```

|     |     | yl)ethylene |
| --- | --- | --- |
| also | (A) | bis-1,1-(indol-3-yl)ethylene |

EXAMPLE 6

Preparation of 3-(4-dimethylaminophenyl)-3-[(4-dimethylaminophenyl)ethyleno-2]-6-dimethylaminophthalide.

This example is also conducted using p-dimethylaminophenyl ethylene, 2-methyl-1-(p-dimethylaminophenyl)ethylene, and 2-phenyl-1-(p-dimethylaminophenyl)ethylene.

Example 6, Summarized.
```
(I)      p-dimethylaminophthalic anhydride
         (T)     p-dimethylaminophenyl
                 (A)    p-dimethylaminophenyl ethylene
                        blue. absorption peak at 735 nanometers
                 also   (A)    1-(p-dimethylaminophenyl)-1-(methoxyphenyl)ethylene
                        (A)    2-bromo-1-(p-dimethylaminophenyl)ethylene
                               blue. absorption shoulder at 830 nanometers,
                               peak at 730 nanometers
also (I) p-di-t-butylaminophthalic anhydride
also (I) 3,4,5,6-tetrabromophthalic anhydride
also (I) 3-methyl phthalic anhydride and 4-butyl phthalic anhydride and
         3-propyl-5-ethyl phthalic anhydride
     (I) 3,4,5,6-tetrachlorophthalic anhydride
         (T)     p-dimethylaminophenyl
                 (A)    p-dimethylaminophenylethylene
                        green. absorption peak at 760 nanometers
                 (A)    2-bromo-1-(p-dimethylaminophenyl)ethylene
                        green. absorption peaks at 770 and 880 nanometers
         also    (A)    p-di-isopentylaminophenylethylene
         also    (A)    1-(p-diisopentylaminophenyl)-1-(carbopentoxy)ethylene
     (I) phthalic anhydride
         (T)     p-dimethylaminophenyl
                 (A)    p-dimethylaminophenylethylene
                        green. absorption peak at 740 nanometers
         (T)     p-diethylaminophenyl
                 (A)    p-dimethylaminophenylethylene
                        green. absorption peak at 740 nanometers
                 (A)    2-bromo-1-(p-dimethylaminophenyl)ethylene
                        green. absorption peak at 730 nanometers
         also    (A)    2-isopropyl-1-(p-diethylaminophenyl)ethylene
         also    (A)    1-(p-diethylaminophenyl)-1-(nitrophenyl)ethylene
also     (T)     2-dimethylamino-4-diethylaminophenyl
also     (T)     2-butylamino-4-dimethylaminophenyl
also     (T)     2-amino-4-dimethylaminophenyl
also     (T)     2-acetamino-4-dimethylaminophenyl
also     (T)     2-bromo-4-dimethylaminophenyl
     (I) quinoxalinic anhydride
         (T)     2-chloro-4-diethylaminophenyl
                 (A)    2-bromo-1-(p-dimethylaminophenyl)ethylene
                        orange. broad absorption peak
         (T)     2-methyl-4-diethylaminophenyl
                 (A)    2-bromo-1-(p-dimethylaminophenyl)ethylene
                        broad absorption peak
         (T)     2-ethoxy-4-dimethylaminophenyl
                 (A)    2-bromo-1-(p-dimethylaminophenyl)ethylene
                        absorption peak at 625 nanometers
also     (T)     2-hexoxy-4-dimethylaminophenyl
```

As a general rule, either carbinol compounds or the corresponding ethylene bases can be used to react with keto acids under the same or similar reaction conditions, in an anhydride reaction medium. In this example, 1.55 grams of 2-(p-dimethylaminobenzoyl)-4-dimethylaminobenzoic acid and 0.82 grams of p-dimethylaminophenylmethyl carbinol are stirred together in 10 milliliters of acetic anydride for two hours at about 56° centigrade. The benzoic keto acid can, for example, be made from a mol-for-mol combination of p-dimethylaminophthalic anhydride (I) and N,N-dimethylaniline (T), as previously described. As previously, the system is extracted with toluene, dried using sodium sulfate, and the toluene is evaporated. The product is isolated using chromatography and a solution of the product imparts a blue color to paper coated with a phenolic resin or silton clay or a combination of the two. A reflection spectrum of the blue color has an absorption peak at 735 nanometers.

EXAMPLE 7

Preparation of 3-(1-ethyl-2-methylindol-3-yl)-3-[bis-1,1-dimethylaminophenyl)ethyleno-2]phthalide.

In this example, 6.17 grams of 1-ethyl-2-methyl-3-(2-carboxybenzoyl)indole, 5.3 grams of bis-1,1-(p-dimethylaminophenyl) ethylene, and 20 milliliters of acetic anhydride are stirred for about 80 minutes at about 65° centigrade. The keto acid of this example can be prepared from a combination of phthalic anhydride with 1-ethyl-2-methylindole alone or the presence of aluminum chloride. The title compound is isolated in the manner previously described and imparts a blue-green color to paper coated with a phenolic resin or silton clay or a combination of the two. A reflectance spectrum of the blue-green color has an absorption peak at 690 nanometers.

This example is also conducted using p-dimethylaminophenylethylene, 2-methyl-1-(p-dimethylaminophenyl)ethylene, bis-1,1-(2-methyl-4-diethylaminophenyl)ethylene, and 2-phenyl-1-(p-dimethylaminophenyl)ethylene.

Example 7, Summarized.
(I)  phthalic anhydride
    (T)  1-ethyl-2-methylindolyl
        (A)  bis-1,1-(p-dimethylaminophenyl)ethylene
            blue-green. broad absorption peak from 575 to 750 nanometers
        (A)  bis-1,1-(2-methyl-4-diethylaminophenyl)ethylene
            green. absorption peak at 720 nanometers
        (A)  2-methyl-bis,1-1-(p-diethylaminophenyl)ethylene
            green. absorption peak at 650 nanometers
        (A)  bis-1,1-(p-methoxyphenyl)ethylene
            red. absorption peak at 570 nanometers
        (A)  p-dimethylaminophenylethylene
            green. absorption peak at 690 nanometers
        (A)  2-bromo-4-dimethylaminophenylethylene
            blue. absorption peaks at 700 and 800 nanometers
also  (T)  1-ethyl-2-methyl-1-H-benz[G]indolyl
also  (T)  2-phenylindolyl
also  (T)  1-phenyl-2-methylindolyl
also  (T)  1-phenylcarbazol-4-yl
also  (T)  7-ethylcarbazol-4-yl
    also  (A)  p-diethylaminophenylethylene
(I)  3,4,5,6-tetrachlorophthalic anhydride
    (T)  1-ethyl-2-methylindolyl
        (A)  bis-1,1-(p-dimethylaminophenyl)ethylene
            blue. absorption peak at 645 nanometers
        (A)  bis-1,1-(p-methoxyphenyl)ethylene
            red. absorption peak at 560 nanometers
        (A)  p-dimethylaminophenylethylene
            red. absorption peak at 740 nanometers
        (A)  2-bromo-4-dimethylaminoethylene
            brown. absorption peak at 700 nanometers
        (A)  bis-1,1-(2-methyl-4-diethylaminophenyl)ethylene
            green. absorption peak at 720 nanometers
also  (T)  1-ethyl-2-methyl-5-hexoxyindolyl
also  (T)  1-hexyl-2-ethylindolyl
    also  (A)  2-bromo-1-(p-dimethylaminophenyl)ethylene
also (I) 3,4,5,6-tetrabromophthalic anhydride
    (T)  1-ethyl-2-methylindolyl
        (A)  2-methyl-bis-1,1-(p-diethylaminophenyl)ethylene
            green. absorption peak at 650 nanometers
        (A)  2-bromo-4-dimethylaminoethylene
            yellow-green. absorption peak at 830 nanometers
also  (T)  2-pentylindolyl
also (I) 3,4-pyridinedicarboxylic acid anhydride
(I)  2,3-pyrazinedicarboxylic acid anhydride
    (T)  1-ethyl-2-methylindolyl
        (A)  2-bromo-4-dimethylaminophenylethylene
            green. absorption peak at 700 nanometers
        (A)  bis-1,1-(2-methyl-4-diethylaminophenyl)ethylene
            green. absorption peak at 700 nanometers
(I)  quinoxalinic anhydride
    (T)  1-ethyl-2-methylindolyl
        (A)  bis-1,1-(p-dimethylaminophenyl)ethylene
            blue. absorption peaks at 645 and 700 nanometers
        (A)  2-methyl-bis-1,1-(p-diethylaminophenyl)ethylene
            green. absorption peak at 650 nanometers
        (A)  2-bromo-4-dimethylaminophenylethylene
            rust. absorption peak at 830 nanometers

EXAMPLE 8

Preparation of 3-(p-diethylaminophenyl)-3-[1-(N-carbazolyl)ethyleno-2]phthalide.

In this example a mol-for-mol combination of phthalic anhydride (I) and N,N-diethylaniline (T) are reacted, as disclosed previously, to yield the keto acid (II). The keto acid is similarly reacted with N-vinyl carbazole to yield the title compound. The title compound imparts a blue-yellow color to paper coated with a phenolic resin or silton clay or a combination of the two. A reflectance spectrum of the blue-yellow color has an absorption peak at 630 nanometers.

This example is also conducted using N-vinylindole and N-vinylpyrrole.

Example 8, Summarized.
(I)  phthalic anhydride
    (T)  p-diethylaminophenyl
        (A)  N-vinylcarbazole
            blue-yellow. absorption peak at 630 nanometers
    (T)  2-methoxy-4-diethylaminophenyl
        (A)  N-vinylcarbazole
            blue-yellow. absorption peak at 610 nanometers
also  (T)  p-dimethylaminophenyl
also  (T)  2-ethoxy-4-dimethylaminophenyl
    (T)  1-ethyl-2-methylindol-3-yl
        (A)  N-vinylcarbazole
            neutral. absorption peaks at 680 and 770 nanometers
(I)  3,4,5,6-tetrachlorophthalic anhydride
    (T)  p-dimethylaminophenyl
        (A)  N-vinylcarbazole
            blue-yellow. absorption peak at 750 nanometers
    (T)  2-methoxy-4-diethylaminophenyl -continued

```
             (A)   N-vinylcarbazole
                       green. absorption peak at 740 nanometers
  also  (T)   p-dimethylaminophenyl
  also  (T)   2-ethoxy-4-dimethylaminophenyl
         (T)   1-ethyl-2-methylindol-3-yl
             (A)   N-vinylcarbazole
                       blue. broad absorption peak
  (I)   2,3-pyridinedicarboxylic acid anhydride
         (T)    1-ethyl-2-methylindol-3-yl
             (A)   N-vinylcarbazole
                       pink. broad absorption peak
  (I)   4-dimethylaminophthalic anhydride
         (T)   p-dimethylaminophenyl
             (A)   N-vinylcarbazole
                       blue. absorption peak at 640 nanometers
```

The gist of this example is the use of N-vinylcarbazole, N-vinylindole and N-vinylpyrrole in the molecule of this invention; and any of the (I) components and any of the (T) components disclosed herein are eligible.

EXAMPLE 9

Preparation of chromogenic compounds based on keto-glutaric anhydride. Either of α-keto-glutaric anhydride or β-keto-glutaric anhydride can be used.

The keto-glutaric anhydride (I) is reacted mol-for-mol with a compound such as 1-ethyl-2-methylindole (T) in the presence of a catalyst, as previously disclosed, to yield keto-acid (II).

The keto-acid (II) is further reacted, in mol-for-mol amounts, with an appropriate ethylene base such as bis-1,1-(dimethylaminophenyl)ethylene to yield a chromogenic compound of this invention.

Mol equivalents of keto-glutaric anhydride (I) and previously-disclosed N,N-dialkylaniline; alkoxy-N,N-dialkylaniline; phenyl-N,N-dialkylaniline; alkyl-N,N-dialkylaniline; chloro- or bromo-N,N-dialkylaniline; indole; alkyl-substituted indole; or phenyl-substituted indole, and the like (T, as a group) yield a keto acid additionally reactive with the previously-disclosed vinyl compounds (A) such as bis-1,1-(p-diethylaminophenyl)ethylene, 2-phenyl-bis-1,1-(p-dimethylaminophenyl) ethylene, N-vinylcarbazole, and the like.

EXAMPLE 10

Preparation of chromogenic compounds based on homophthalic anhydride.

Homophthalic anhydride (I) can be reacted mol-for-mol with a compound such as 1-ethyl-2-methylindole (T) in the presence of a catalyst, as previously disclosed, to yield keto-acid (II).

The keto-acid (II) is further reacted, in mol-for-mol amounts, with an appropriate ethylene base such as bis-1,1-(dimethylaminophenyl)ethylene to yield a chromogenic compound of this invention.

Mol equivalents of homophthalic anhydride (I) and previously-disclosed N,N-dialkylaniline; alkoxy-N,N-dialkylaniline; phenyl-N,N-dialkylaniline; alkyl-N,N-dialkylaniline, chloro- or bromo-N,N-dialkylaniline; indole; alkyl-substituted indole; or phenyl-substituted indole, and the like, (T, as a group) yield a keto acid additionally reactive with the previously-disclosed vinyl compounds (A) such as bis-1,1-(p-diethylaminophenyl)ethylene, 2-phenyl-bis-1,1-(p-dimethylaminophenyl)ethylene, N-vinylcarbazole, and the like.

EXAMPLE 11

Preparation of chromogenic compounds based on biphenyl-4,4'-dicarboxylic anhydride.

The biphenyl-4,4'-dicarboxylic anhydride (I) can be reacted mol-for-mol with a compound such as 1-ethyl-2-methylindole (T) in the presence of a catalyst, as previously disclosed, to yield keto-acid (II).

The keto-acid (II) is further reacted, in mol-for-mol amounts, with an appropriate ethylene base such as bis-1,1-(dimethylaminophenyl)ethylene to yield a chromogenic compound of this invention.

Mol equivalents of biphenyl-4,4'-dicarboxylic anhydride (I) and previously-disclosed N,N-dialkylaniline; alkoxy-N,N-dialkylaniline; phenyl-N,N-dialkylaniline; alkyl-N,N-dialkylaniline; chloro- or bromo-N,N-dialkylaniline; indole; alkyl-substituted indole; or phenyl-substituted indole (T, as a group) yield a keto acid additionally reactive with the previously-disclosed vinyl compounds (A) such as bis-1,1-(p-diethylaminophenyl)ethylene, 2-phenyl-bis-1,1-(p-dimethylaminophenyl)ethylene, N-vinylcarbazole, and the like.

What is claimed is:

1. A compound represented by the formula:

wherein E is:

unsubstituted and alkyl-, cloro-, dichloro-, trichloro-, tetrachloro-, bromo-, dibromo-, tribromo-, tetrabromo-, nitro-, and dialkylamino- substituted;

, unsubstituted and nitro-substituted;

and

A is: a CH=CH group with X and Y substituents and H;

X is: a phenyl ring substituted with R₃, R₄, R₅, R₆ and N(R₁)(R₂);

4-alkoxyphenyl; 2,4-dialkoxyphenyl and 3,4-dialkoxyphenyl;

Y is: any X; hydrogen; carbalkoxy; and nitro;

$R_1$ and $R_2$ are: hydrogen, alkyl, unsubstituted phenyl, substituted phenyl, benzyl, acyl, and cycloalkyl; but $R_1$ and $R_2$ are not both phenyl;

$R_3$, $R_4$, $R_5$, and $R_6$ are: hydrogen, alkyl, phenyl, benzyl, alkoxy, halo, dialkylamino, monoalkylamino, amino and acylamino.

2. The compound of claim 1 wherein X and Y are a cyclohexane ring substituted with R₃, R₄, R₅, R₆ and N(R₁)(R₂).

3. The compound of claim 1 wherein X is a cyclohexane ring substituted with R₃, R₄, R₅, R₆ and N(R₁)(R₂)

and Y is hydrogen.

4. The compound of claim 2 wherein $R_1$ and $R_2$ are alkyl.

5. The compound of claim 4 wherein $R_3$ in other than the X and Y moieties is alkoxy and $R_3$ in the X and Y moieties, $R_4$, $R_5$ and $R_6$ are hydrogen.

6. The compound of claim 4 wherein $R_3$, $R_4$, $R_5$ and $R_6$ are hydrogen.

7. The compound of claim 6 wherein $R_1$ and $R_2$ are ethyl and E is a phenyl group.

8. The compound of claim 6 wherein $R_1$ and $R_2$ are ethyl and E is a phenyl group substituted with N(C₂H₅)₂.

9. The compound of claim 6 wherein $R_1$ and $R_2$ are methyl and E is a cyclohexyl group substituted with N(CH₃)₂.

10. The compound of claim 4 wherein $R_3$ is alkyl.

11. The compound of claim 4 wherein $R_3$ in the X and Y moieties is alkyl.

12. The compound of claim 11 wherein $R_3$ in other than the X and Y moieties is alkoxy.

* * * * *

UNITED STATES PATENT AND TRADEMARK OFFICE
CERTIFICATE OF CORRECTION

PATENT NO. : 4,022,771
DATED : May 10, 1977
INVENTOR(S) : Sheldon Farber

It is certified that error appears in the above-identified patent and that said Letters Patent are hereby corrected as shown below:

Claim 1, column 18, line 57, change "cloro" to ---chloro---.

Each of claims 2 and 3, change

Claim 9, change

Signed and Sealed this

Fifteenth Day of November 1977

[SEAL]

Attest:

RUTH C. MASON
Attesting Officer

LUTRELLE F. PARKER
Acting Commissioner of Patents and Trademarks